United States Patent [19]

Dorn et al.

[11] 4,144,133

[45] Mar. 13, 1979

[54] FUNGAL GROWTH MEDIA

[75] Inventors: Gordon L. Dorn, Dallas; Geoffrey A. Land, Denton, both of Tex.

[73] Assignee: J. K. and Susie L. Wadley Research Institute and Blood Bank, Dallas, Tex.

[21] Appl. No.: 827,573

[22] Filed: Aug. 25, 1977

[51] Int. Cl.$^2$ .............................................. C12K 1/06
[52] U.S. Cl. ............................ 195/100; 195/103.5 M
[58] Field of Search ................ 195/103.5 M, 100, 101, 195/102

[56] References Cited

U.S. PATENT DOCUMENTS

| | | | |
|---|---|---|---|
| 3,345,270 | 10/1967 | Gray | 195/100 |
| 3,649,460 | 3/1972 | Controni et al. | 195/100 |

OTHER PUBLICATIONS

Fleming et al., Journal of Clinical Microbiology, Feb. 1977, vol. 5, No. 2, pp. 236–243.

*Primary Examiner*—Alvin E. Tanenholtz
*Attorney, Agent, or Firm*—Richards, Harris & Medlock

[57] ABSTRACT

Fungal growth media comprising a mixture of oxgall, purified saponin, a substrate for phenol oxidase and a supporting agent, such as agar, are provided which facilitate rapid identification of a variety of pathogenic fungi obtained from a sample of body fluid, for example. Specifically, the growth media of the present invention provides for the rapid differential identification of *Candida albicans* and *Cryptococcus neoformans*.

16 Claims, No Drawings

FUNGAL GROWTH MEDIA

BACKGROUND OF THE INVENTION

In one aspect, the present invention relates to fungal growth media comprising oxgall, purified saponin, a substrate for phenol oxidase and a supporting agent therefor, such as agar, for example. In another aspect, this invention relates to a differential medium for the detection and identification of pathogenic yeast-type fungi. In still another aspect, the present invention relates to storable dry fungal media preparations which, upon addition of water, provide growth media useful in a rapid differential analysis for several of the more common pathogenic fungi present in body fluid samples. In still a further aspect, the fungal media of the present invention provide an especially rapid and reliable technique for the detection of, and differentiation of, two medically important fungi, *Candida albicans* and *Cryptococcus neoformans*.

Under normal conditions, various types of yeasts (that is, single cell fungi) will be present in the body as saprophytes and will not interrupt normal body functioning because the fungal growth will be controlled by normal types of bacteria which are also present. However, when a patient is treated for bacterial infections, through the use of antibacterial antibiotics for example, the normal bacterial-fungal balance will be disrupted and fungal infection becomes a real possibility. Cancer patients, because of the multiple antibacterial drugs administered and because of an incompetent immune system, are especially susceptible to fungal infection. Fungal infection can cause a rapid deterioration of the patient's condition, especially if the patient is already in a weakened state resulting from bacterial infections, for example. Such fungal infections can precipitate serious conditions, for example, meningitis.

Two of the most medically important types of fungi are *Candida albicans* and *Cryptococcus neoformans*. *Candida albicans* is a saprophyte found in the gastrointestinal tract of man. Under certain conditions, however, this yeast may become invasive causing a severe and usually fatal disease in the debilitated patient. *Cryptococcus neoformans* is especially important because of its predilection for the central nervous system which can cause severe disease in a biologically defenseless patient.

The presumptive identification of *Candida albicans* depends solely upon morphological changes which occur when this fungus is plated and allowed to grow on an appropriate medium. The first morphological change indicative of the presence of *Candida albicans* is the formation of germ tubes, which appear as tiny appendages extending from the plated unicellular specimens. These germ tubes eventually grow into elongated filaments extending outwardly from the body of the *Candida albicans*. Formation of germ tubes within 2 to 3 hours after plating of the fungus is presumptive evidence that *Candida albicans* is present. In a second stage of growth, generally round bodies appear at the ends of the filaments. These round bodies are known as chlamydospores. Only two species of the *Candida* genus will form chlamydospores. These are *Candida albicans* and *Candida stellatoidea*. Thus, chlamydospore formation is indicative of the presence of either *Candida albicans* or *Candida stellatoidea*.

Identification of *Cryptococcus neoformans* is generally recognized to be more difficult than the identification of *Candida albicans* in that *Cryptococcus neoformans* undergoes no morphological changes which can be observed and remains unicellular throughout its growth patterns. Until recently, one or more of three basic tests, or a combination thereof, were employed to identify the presence of the genus *Cryptococcus*. One of the methods of identification comprises microscopic inspection of a specimen to identify whether or not a capsule-like formation around the cells of the fungi is present. In order to aid in the inspection of such capsule-like formations, a specimen is surrounded with india ink which enhances the appearance of the capsule by providing a clear and translucent image against the black background making such capsules easier to identify during microscopic examination. A second method employed to identify the genus *Cryptococcus* comprises plating the specimen in a medium containing urea and a color indicator. Because *Cryptococcus neoformans* produces an enzyme known as urease it has the capability to break down and use the nitrogen contained in the urea, causing the pH to rise, thereby changing the color of the indicator. Therefore, growth on a urea containing medium is indicative of the presence of *Cryptococcus neoformans*. A third method for the identification of the genus *Cryptococcus* relies on the ability of that genus to produce a starch-like compound. When the starch-like compound is present addition of iodine will cause a purple ring to appear around the colony. It is to be noted that neither of these tests is specific for *Cryptococcus neoformans* by itself or in combination, as other species within the genus *Cryptococcus* and other genera of yeasts may also give a positive reaction.

Therefore, in order to identify the species *Cryptococcus neoformans* additional tests have had to be employed in the past. These include the development of a growth profile of a specimen when plated on a series of carbohydrate containing media. For example, up to fourteen different types of carbohydrates can be incorporated into growth media and after 7 to 21 days a specimen plated thereon will develop a growth profile which will indicate whether or not *Cryptococcus neoformans* is possibly present in the specimen. Another method for identifying the species is to plate the fungal sample on an agar medium containing creatinine and if significant growth is observed within 5 to 8 days such growth is indicative of the presence of *Cryptococcus neoformans* because of that fungi's capability to assimiliate the creatinine. However other genera of yeast can also grow on creatinine so this test is not specific for *Cryptococcus neoformans*.

Perhaps the single most successful and specific conventional test for *Cryptococcus neoformans* includes the use of bird seed agar. It was discovered that if *Cryptococcus neoformans* was present in a sample plated on bird seed agar a specific tell-tale brown color would appear, as the specimen grew on the plate, within a period of five days to two weeks. This method was improved by employing an extract of bird seed which lowered the identification time 3 to 5 days. Later it was discovered that the brown pigment coloration was the result of the reaction between the enzyme phenol oxidase and a particular substrate present in bird seed agar. Accordingly, use of substituted phenols such as caffeic acid in the growth medium further shortened the period of time necessary for identification to about forty-eight hours. A still further refinement of the use of caffeic acid to identify *Cryptococcus neoformans* is set forth in an article by Hopfer and Groschel entitled "Six Hour Pigmentation Tests for the Identification of *Cryptococcus Neoformans*", Journal of Clinical Microbiology, August 1975, Vol. II, No. 2, p. 96–98. The improvement set forth therein includes combining caffeic acid with ferric citrate and incorporating these compounds onto paper discs for use as substrates for the phenol oxidase enzyme activity of *Cryptococcus neoformans*. Use of these caffeic acid-ferric citrate impregnated paper discs further lowered the identification time to 3 to 6 hours. However, the solution of caffeic acid and ferric citrate used to impregnate the paper discs is quite unstable when exposed to light and therefore presents serious storage problems. Furthermore, the relative concentrations of caffeic acid and ferric citrate are critical and an unbalanced combination will require longer incubation periods for production of a dark pigment, or, in some cases, nonspecific pigmentation of saprophytic *Cryptococcus* species and several *Candida* species. Furthermore, while identification times are lowered to 3 to 6 hours from the time of plating onto the paper discs the sample must be grown on a "primary" medium before plating onto the ferric citrate, caffeic acid impregnated discs.

It should be noted that, while *Candida albicans* and *Cryptococcus neoformans* are two of the most medically important yeasts, no conventional test procedure or medium can be employed to simultaneously identify the presence of both of these fungi. Instead, it has been necessary in the past to run two tests, one for the presence of *Candida albicans* and a second test, such as one of those described above, to identify *Cryptococcus neoformans*.

Recently a new culture medium for the identification of *Cryptococcus neoforms*, *Candida albicans* and *Candida stellatoidea* was discovered which includes caffeic acid, oxgall and an emulsifying agent sold under the tradename Tween 80 by Atlas Chemical Company. This medium is described by Fleming, Hopkins and Land in an article entitled, "New Culture Medium for the Presumptive Identification of *Candida albicans* and *Cryptococus neoformans*," Journal of Clinical Microbiology, February 1977, Vol. V, No. 2, p. 236–243 and provides for the specific identification of both *Candida albicans* and *Cryptococcus neoformans*. While identification of *Cryptococcus neoformans* is slower than when the caffeic acid-ferric citrate impregnated paper discs discussed above are employed the Tween 80, oxgall, caffeic acid medium (hereinafter sometimes referred to as TOC) has certain advantages in that it is not light sensitive and the concentration of components do not have to be as critically formulated as the ferric-citrate discs. The only disadvantage of the TOC medium is that *Candida krusei*, a filamenting yeast, will not form pseudohyphae. Thus, while the presence of *Candida albicans* or *Candida stellatoidea* can be determined by the formation of germ tubes within 3 hours of plating, the presence of *Candida krusei* may remain undetected as no filamentation appears even after 24 hours on TOC medium. Further, while the shelf life of prepared TOC medium is good (about 2 to 3 weeks) a longer shelf life is, of course, desirable. In addition, because Tween 80 is a liquid composition, TOC medium does not lend itself to the formulation of a completely dehydrated dry powder composition easily storable in powdered form for preparation and use as needed. This medium does, however, provide for a single test procedure which will identify the presence of *Candida albicans*, *Candida stellatoidea* and *Cryptococcus neoformans*.

Thus, while a variety of methods and media have been employed in order to identify and differentiate various fungal pathogens including the important species *Candida albicans* and *Cryptococcus neoformans*, there is a continuing need for fungal growth media which will rapidly identify and differentiate those species as well as other opportunistic fungi and which are relatively easy to prepare and use and which have a relatively long shelf life.

BRIEF DESCRIPTION OF THE INVENTION

According to the present invention, a fungal growth medium is provided which rapidly and reliably identifies fungi which can be pathogenic under certain conditions such as for example, in patients receiving immunosuppressant drugs. Basically, the fungal media of the present invention comprise oxgall, purified saponin, a phenol oxidase substrate and a supporting agent. The phenol oxidase substrate, preferably in the form of caffeic acid, provides for the specific identification of *Cryptococcus neoformans* by means of the appearance of the characteristic brown pigmentation which results from specific enzyme activity of *Cryptococcus neoformans* on the phenol oxidase substrate. The oxgall, in addition to its known function of suppressing nonpathogenic organisms, has also been discovered to enhance filament and chlamydospore production of the medically important fungi *Candida albicans* and *Candida stellatoidea*. The purified saponin employed in the fungal media of the subject invention significantly increases the tell-tale brown pigmentation of *Cryptococcus neoformans* and enhances the germ tube and chlamydospore production of *Candida albicans* and *Candida stellatoidea* thus providing for extremely rapid identification of these especially serious types of pathogenic fungi. The carrying agent, such as common agar or silica gels for example, simply provides a supporting base for the above described active ingredients.

DETAILED DESCRIPTION OF THE INVENTION

The growth media of the present invention provides an excellent differential medium for the identification of two of the most medically important types of potentially pathogenic fungi. The media of the present invention are specific for the identification of *Cryptococcus neoformans* and rapidly indicate the presence of either the *albicans* or *stellatoidea* species of the genus *Candida*. Differentiation between these two species of *Candida* may be accomplished by performing an additional conventional differentiation test such as an assimilation test for the sugar sucrose, wherein *Canadida albicans* will assimilate sucrose and *Candida stellatoidea* will not. In addition, the growth media of the subject invention are useful in the identification of the other genera of filamenting yeasts by permitting characteristic morphology and pigmentation to remain unaltered. For example, *Candida krusei* and *Candida tropicalis* remain as white filamenting yeasts upon the media of the subject invention.

The major advantage of employing the differential media of the present invention is the rapidity and specificity of the medium in the identification of *Cryptococcus neoformans* and *Candida albicans*. Thus, *Cryptococcus neoformans* may be identified within 3 to 6 hours after plating a sample on the growth media of the subject invention, the identification being made possible by the tell-tale brown pigmentation observable with the naked eye within this time period. The presence of *Candida albicans* or *Candida stellatoidea* can be determined within from about 3 to about 18 hours of plating at which time germ tubes and chlamydospores, respectively, will be visible upon microscopic inspection. Since only the *albicans* and *stellatoidea* species of the genus *Candida* form germ tubes and chlamydospores, a single conventional differential test can be performed to identify which of the species is present.

It has been discovered that a combination of three active ingredients can be employed, with a supporting medium such as agar, for example, to effect the above described desirable results. Oxgall, a derivative of a substance found in the gall bladder of oxen, is employed in order to promote the growth of filaments and chlamydospores of *Candida albicans* and *stellatoidea*. A second ingredient, such as caffeic acid or some other substrate of phenol oxidase enzymes, is employed as an identification agent for *Cryptococcus neoformans* since the reaction of the phenol oxidase enzymes of that fungus with such a substrate produce a brownish pigmentation which is specific for *Cryptococcus neoformans*. The third active ingredient employed in the fungal media of the present invention is purified saponin. Generally, saponins are glycosides widely distributed in plants and are capable of forming oil-in-water emulsions and acting as protective colloids. Each saponin molecule consists of a sapogenin which constitutes the aglucone moiety of the molecule, and sugar. It is important to note that only purified saponins can be employed in order to obtain the desired results. Purified saponin, unlike unpurified saponin, is nontoxic to microbial pathogens such as the yeasts which are identified using the media of the present invention. Generally, saponins may be purified using the techniques set forth in U.S. Pat. No. 3,883,425 entitled "DETOXIFICATION OF SAPONINS", issued May 13, 1975, and the purified saponins can then be employed in the fungal media of the present invention. While the exact function of the saponin present in the fungal media of the subject invention is not known, it is theorized that the saponin has an emulsifying effect which tends to separate individual fungal cells from clusters of cells present in a body fluid sample. The separation is believed to aid in the reaction of the phenol oxidase substrate with the phenol oxidase enzymes of *Cryptococcus neoformans* thus providing for more rapid development of the characteristic brown pigmentation.

The phenol oxidase substrate employed in the fungal media of the present invention can be selected from any of a known group of substrates which are known to produce brown pigmentation in the presence of *Cryptococcus neoformans*. Suitable phenol oxidase substrates include 2,3-dihydroxybenzoic acid, 3,4-dihydroxybenzoic acid (protocatechuic acid), DOPA, 3,4-dihydroxycinnamic acid (caffeic acid), the methyl ester and diacetate of caffeic acid, 3hydroxytryptamine, 3,4-dihydroxyphenylethanolamine (norepinephrine), and 4-hydroxy-3,5-dimethoxycinnamic acid. It is believed that the coloration is dependent upon the hydroxyl groups in the 3,4 positions of the phenyl ring. Of the above mentioned phenol oxidase substrates, the preferred substrate is caffeic acid.

The fungal media of the present invention can be prepared in the following manner. The oxgall, purified saponin and the phenol oxidase substrate can be added with an appropriate amount of a powdered supporting agent, such as agar, for example, to distilled water. The resulting mixture is then stirred and heated to boiling to allow the components to go into solution. The solution is then sterilized at approximately 121 degrees C. at about 15 psi pressure for approximately 15 minutes. After sterilization and slight cooling the medium can be poured into conventional type petri dishes and, after solidification, the plates can be inverted and allowed to dry overnight at room temperature. The resulting petri dishes can then be refrigerated for storage and have useful shelf lives of up to about 6 weeks.

Generally, the fungal media of the present invention comprises from about 0.25 to about 30 weight percent oxgall, from about 1 to about 5 weight percent of a supporting agent, from about 0.1 to about 5.0 weight percent purified saponin, and from about 0.001 to about 1.0 weight percent of a phenol oxidase substrate, based on the amount of water added to these components.

Preferred media can be prepared by following the procedure outlined above and employing from about 0.5 to about 5 weight percent of oxgall, from about 1 to about 5 weight percent of agar, from about 0.1 to about 1.0 weight percent of purified saponin and from about 0.005 to about 0.05 weight percent caffeic acid, based on the amount of water added to the dry components. A most preferred medium contains about 1.0 weight percent oxgall, about 2.0 weight percent agar, about 0.5 weight percent purified saponin and about 0.03 weight percent caffeic acid. It should be noted that one of the advantages of the fungal media of the present invention is that all of the components (except water) are in a powdered form so that premeasured amounts of each component can be combined to form a fungal medium preparation which can be stored indefinitely in a dry state and then prepared, as needed, by addition of water following the above outlined conventional procedures.

The fungal media of the present invention can be employed either as a primary or secondary plating medium for the relatively rapid differential identification of *Cryptococcus neoformans* and *Candida stellatoidea*. When used as a primary medium a sample of body fluid (such as blood, sputum or urine, for example) is plated directly onto the SOC media and subjected to a proper environment for fungal growth. In the secondary plating method, the sample of body fluid is first plated on a primary media, such as Sabouraud agar, which provides for fairly rapid initial growth of any fungi present, and, after such initial growth has occurred, the fungi are streaked onto the SOC media of the present invention which rapidly provides for the differentiation of various fungal species.

EXAMPLES

The following examples demonstrate the advantage of the fungal media of the present invention over those previously employed for the identification of various fungi, including *Candida albicans, Candida stellatoidea* and *Cryptococcus neoformans*. These examples are submitted for the purpose of providing a better understanding of the present invention and are not to be construed as limiting the scope thereof.

EXAMPLE I

This example was performed in order to compare the time required for characteristic morphological changes to occur in fungi plated on corn meal agar (CMA), a media comprising caffeic acid, oxgall and Tween 80 (TOC) and the fungal media of the present invention which comprises a mixture of purified saponin, oxgall, and caffeic acid (SOC).

The CMA was made up according to the manufacturer's directions and supplemented with 0.1% Tween 80. The TOC medium, consisting of Tween 80, oxgall, caffeic acid, and Davis agar, was prepared as follows: to 1 liter of distilled water was added 10 grams of oxgall, 20 grams of agar, 10 mls of a 10% solution of Tween 80, and 0.3 grams of caffeic acid. The mixture was stirred, heated to boiling to allow the components to go into solution, and sterilized at approximately 120 degrees C. at about 15 psi of pressure for 15 mins. After sterilization and slight cooling the medium was then poured into petri dishes. The test medium of the present invention, SOC, was prepared as follows: 10 grams of oxgall, 20 grams of agar, 5 grams of purified saponin and 0.3 grams of caffeic acid were added to 1 liter of distilled water. The mixture was stirred, heated to boiling to allow the components to go into solution, and sterilized at 120 degrees C. at 15 psi of pressure for 15 mins. After sterilization and slight cooling, this medium was poured into petri dishes to allow solidification to occur.

Stock yeast strains were subcultured onto Sabouraud dextrose agar and allowed to grow for 72 hrs. After this preliminary growth, a means for simulating growth on a primary plate, yeasts were subcultured by the Dalmau technique onto either the CMA, TOC, or SOC mediums. This technique is simply the placing of a cover-slip over an area inoculated with organisms, permitting one to microscopically view the inoculated areas of the plate. To obtain a heavy inoculum, a sterile swab was used to make a sweep of the colonies on the Sabouraud dextrose agar plates.

Table 1 sets forth the results of the tests performed in order to compare the time required for chlamydospore production of *Candida albicans* on CMA, TOC, and SOC. One hundred and thirty-eight isolates of *Candida albicans* were plated and observed at the time intervals specified in Table 1. The number of chlamydospores produced per 100 X microscope field were then recorded for each of the media. All of the isolates run on each media were subjected to substantially identical environments.

TABLE 1

Comparison of Time Required for Chlamydospore Production of *Candida albicans* on CMA, TOC, SOC Media

| Time of Observation (Hours) | CMA | TOC | SOC |
|---|---|---|---|
| 12 | — | A | A |
| 14 | — | A | B |
| 16 | — | A-B | D |
| 18 | — | B-C | D |
| 20 | — | C-D | D |
| 24 | A | C-D | D |
| 48 | A | D | D |

A = 1 to 4 chlamydospores/100X field
B = 5 to 20 chlamydospores/100X field
C = 21 to 50 chlamydospores/100X field
D = 50 or more chlamydospores/100X field As can be seen from a study of Table 1, chlamydospore production on the SOC medium reached its maximum after only 16 hours. In contrast, chlamydospore production on the TOC medium did not approach its maximum level until 20 hours. The chlamydospore production on CMA was significantly inferior to that of both the TOC and SOC mediums.

TABLE 2

Comparative Production of Germ Tubes and Chlamydospores on Dalmau* Slide Cultures Using CMA, TOC and SOC Plates

| Organism | No. of Isolates | Medium | Germ Tube Formation | | Chlamydospore Production | | | | | |
|---|---|---|---|---|---|---|---|---|---|---|
| | | | | | 24 hrs. | | 48 hrs. | | 72 hrs. | |
| | | | No. | % | No. | % | No. | % | No. | % |
| *Candida albicans* | 138 | CMA | 0 | 0.0 | 25 | 8.1 | 84 | 60.9 | 112 | 81.2 |
| | | TOC | 132 | 95.7 | 119 | 86.2 | 133 | 96.3 | 134 | 97.1 |
| | | SOC | 138 | 100.0 | 138 | 100.0 | 138 | 100.0 | 138 | 100.0 |
| *Candida stellatoidea* | 30 | CMA | 0 | 0.0 | 0 | 0.0 | 0 | 0.0 | 0 | 0.0 |
| | | TOC | 24 | 80.0 | 24 | 80.0 | 24 | 80.0 | 24 | 80.0 |
| | | SOC | 24 | 80.0 | 24 | 100.0 | 24 | 100.0 | 24 | 100.0 |

*Dalmau Slide Culture: The placing of a sterile cover slip over a streaked portion of the organism, allowing growth and morphology to be determined by scanning the plate with a microscope.

The SOC media of the present invention was also compared to CMA and TOC on the basis of germ tube formation and chlamydospore production over a period of 72 hours. Two different species of *Candida* were compared on each media. The results of these tests are set forth in Table 2 below.

The data set forth in Table 2 indicates that the SOC media has a distinct advantage over TOC media in the formation of germ tubes and chlamydospore production for *Candida albicans*. Both of these media demonstrated a marked superiority over the results obtainable with CMA. With regard to the data set forth in Table 2 with respect to *Candida stellatodia*, the SOC and TOC media preformed virtually identically, both of these media having a marked superiority over the CMA media.

Finally, the specificity of the SOC media for *Cryptococcus neoformans* was tested by plating a number of strains of eight different types of fungi in order to determine whether or not the characteristic brown pigmentation would be specific for *Cryptococcus neoformans*. As can be seen from Table 3 below, the brown pigmentation occurred, on an average, at approximately 5.3 hours when *Cryptococcus neoformans* was plated on the SOC medium of the present invention. None of the other seven fungi tested produced any noticeable pigmentation after 72 hours of growth.

TABLE 3

Pigment Production on SOC Medium

| Organism | No. Strains | Pigment | Average Time To Change |
|---|---|---|---|
| *Cryptococcus neoformans* | 70 | Brown | 5.3 hr. |
| *Candida albicans* | 138 | White | NC[1] |
| *Candida stellatoidea* | 30 | White | NC |
| *Candida tropicalis* | 40 | White | NC |
| *Cryptococcus laurentii* | 40 | White | NC |
| *Cryptococcus innocuous* | 17 | White | NC |
| *Cryptococcus diffluens* | 8 | White | NC |
| *Torulopsis glabrata* | 73 | White | NC |

[1]NC = No Change in Pigmentation After 72 Hour Growth

EXAMPLE II

In order to compare the purified saponin, oxgall, caffeic acid media of the present invention with the Tween 80, oxgall, caffeic acid types of media discussed above, samples of each of these types of media were prepared varying the relative proportions of the three active ingredients. A large inoculum of *Candida albicans, Candida stellatodia, Candida tropicalis, Candida*

*krusei, Cryptococcus neoformans,* and *Cryptococcus diffluens* were then plated via a cotton swab onto the various test medias and observed at intervals of 3 and 24 hours. In the case of the *Candida* organisms, the morphological changes occurring at each of the inspection intervals was recorded. Thus, the percentage of isolates of each organism demonstrating the morphological changes of germ tube production (gt), filament production (F) and filament and chlamydospore production (FC), and Pseudohyphae (PSH) were recorded for each of the test media. For the *Cryptococcus* organisms, the number of isolates demonstrating a visible pigmentation change was recorded as a percentage of the total number of isolates tested, the inspection for pigmentation also being made at intervals of 3 and 24 hours in each case. The results of these test media comparisons are set forth in Table 4 below.

logical changes of the *Candida* genus, or the pigmentation changes of the *Cryptococcus* genus, or both.

Samples 12-15 demonstrate that when the oxgall and caffeic acid contents of the medias are held at a constant level and the purified saponin content is varied within a range of from 5 to 100 grams/liter good results can be obtained. However, it will be noted from a study of Samples 12-15 that the amount of pigmentation of the *Cryptococcus neoformans* is at its maximum at the 3 hr. observation when only 5 grams of purified saponin is employed, whereas addition of more saponin does not improve the pigmentation change.

Samples 16-20 demonstrate that various amounts of caffeic acid can be used in combination with oxgall and purified saponin. However, it should be noted that at amounts less than about 0.25 grams/liter the caffeic acid is present in insufficient amounts to cause the desirable

TABLE 4

| Sample No. | Agar g/l | Oxgall g/l | Caffeic Acid g/l | Tween 80 g/l | Purified Saponin g/l | Hrs. | Candida albicans | Candida stellatoidea | Candida tropicalis | Candida krusei | Cryphococcus neoformans | Cryphococcus diffluens |
|---|---|---|---|---|---|---|---|---|---|---|---|---|
| (1) | 20 | 10 | 0.3 | — | — | 3 | 30% gt | 80% gt | — | — | — | — |
|  |  |  |  |  |  | 24 | 100% F | 100% FC | 100% F | 40% F | 100% | — |
| (2) | 20 | — | 0.3 | 10 | — | 3 | — | 40% gt | — | — | — | — |
|  |  |  |  |  |  | 24 | 20% F | 10% FC 50% F | — | — | 100% | — |
| (3) | 20 | — | 0.3 | — | 10 | 3 | 100% gt | 25% gt | — | — | — | — |
|  |  |  |  |  |  | 24 | 60% F | 50% F | — | — | 100% | 10% |
| (4) | 20 | 0.25 | 0.3 | 10 | — | 3 | 40% gt | 100% gt | — | — | — | — |
|  |  |  |  |  |  | 24 | 20% FC 60% F | 90% FC | 100% F | — | 100% | — |
| (5) | 20 | 0.25 | 0.3 | — | 10 | 3 | 100% gt | 100% gt | — | — | — | — |
|  |  |  |  |  |  | 24 | 60% F | 50% F | 100% F | — | 100% | 10% |
| (6) | 20 | 1.25 | 0.3 | 10 | — | 3 | 100% gt | 100% gt | — | — | — | — |
|  |  |  |  |  |  | 24 | 80% FC | 90% FC | 100% F | 30% F | 100% | — |
| (7) | 20 | 1.25 | 0.3 | — | 10 | 3 | 100% gt | 100% gt | — | — | — | — |
|  |  |  |  |  |  | 24 | 100% FC | 100% FC | 100% F | 10% F | 100% | — |
| (8) | 20 | 2.5 | 0.3 | 10 | — | 3 | 60% gt | 100% gt | — | — | — | — |
|  |  |  |  |  |  | 24 | 100% FC | 80% FC | 100% F | 90% F | 100% | 100% |
| (9) | 20 | 2.5 | 0.3 | — | 10 | 3 | 100% gt | 100% gt | — | — | 20% | — |
|  |  |  |  |  |  | 24 | 100% FC | 100% FC | 100% F | 40% F | 100% | 50% |
| (10) | 20 | 5.0 | 0.3 | 10 | — | 3 | 60% gt | 90% gt | — | — | 50% | 50% |
|  |  |  |  |  |  | 24 | 100% FC | 100% FC | 100% FC | 80% F | 100% | 100% |
| (11) | 20 | 5.0 | 0.3 | — | 10 | 3 | 100% gt | 100% gt | — | — | 20% | — |
|  |  |  |  |  |  | 24 | 100% gt | 100% FC | 100% F | 100% F | 100% | 100% |
| (12) | 20 | 10 | 0.3 | — | 5 | 3 | 100% gt | 80% gt | — | — | 60% | — |
|  |  |  |  |  |  | 24 | 100% FC | 100% FC | 100% F | 90% F | 100% | — |
| (13) | 20 | 10 | 0.3 | — | 10 | 3 | 100% gt | 100% gt | — | — | 50% | — |
|  |  |  |  |  |  | 24 | 100% FC | 100% FC | — | 100% F | 100% | — |
| (14) | 20 | 10 | 0.3 | — | 50 | 3 | 100% gt | 100% gt | — | — | 90% | — |
|  |  |  |  |  |  | 24 | 100% FC | 100% FC | — | 100% F | 100% | — |
| (15) | 20 | 10 | 0.3 | — | 100 | 3 | 100% gt | 100% gt | — | — | 20% | — |
|  |  |  |  |  |  | 24 | 100% FC | 100% FC | 100% F | 100% F | 100% | — |
| (16) | 20 | 2.5 | 0.025 | — | 10 | 3 | 100% gt | 100% gt | — | — | — | — |
|  |  |  |  |  |  | 24 | 100% FC | 100% FC | 100% F | 20% F | — | — |
| (17) | 20 | 2.5 | 0.25 | — | 10 | 3 | 100% gt | 100% gt | — | — | — | — |
|  |  |  |  |  |  | 24 | 100% FC | 100% FC | 100% F | 60% F | — | — |
| (18) | 20 | 2.5 | 2.50 | — | 10 | 3 | 100% gt | 100% gt | — | — | — | — |
|  |  |  |  |  |  | 24 | 100% FC | 100% FC | 100% F | 100% F | 100% | — |
| (19) | 20 | 2.5 | 12.50 | — | 10 | 3 | 100% gt | 100% gt | — | — | — | — |
|  |  |  |  |  |  | 24 | 100% FC | 100% FC | 100% F | 100% F | 100% | — |
| (20) | 20 | 2.5 | 25.00 | — | 10 | 3 | 100% gt | 100% gt | — | — | 30% PSH | — |
|  |  |  |  |  |  | 24 | 90% FC | 60% FC | 100% F | 100% F | 100% | — |

Sample 1 in Table 4 records the results when neither Tween 80 nor purified saponin are employed in an oxgall-caffeic acid medium. In Samples 2-11 the amount of caffeic acid was held constant, while the amount of oxgall was varied upward, at intervals of two samples, from a range of 0 (in Samples 2 and 3) to 5 grams/liter (in Samples 10 and 11). For each pair of samples having the same amount of oxgall, one employed Tween 80 in combination with the oxgall and caffeic acid (the even numbered samples) and the other employed purified saponin, in accordance with the invention of the present application (odd numbered samples). In both cases, 10 grams/liter of Tween 80 or purified saponin was employed. A study of the Samples 2-11 demonstrates the superiority of the SOC medium of the present invention as compared to the TOC media in either the morphological pigmentation changes within either the 3 or 24 hr. observation periods.

While the present invention has been described in relation to its preferred embodiments, it is to be understood that various modifications thereof will be apparent to one skilled in the art upon reading the specification and it is intended to cover such modifications as fall within the scope of the appended claims.

We claim:

1. A fungal growth medium comprising oxgall, purified saponin which is nontoxic to microbial pathogens, and a substrate for phenol oxidase in combination with a supporting agent therefore.

2. The fungal growth medium of claim 1 wherein said substrate for phenol oxidase is selected from the group consisting of 2, 3-dihydroxybenzoic acid, protocatechuic acid, DOPA, caffeic acid, the methyl ester of caffeic acid, the diacitate of caffeic acid, 3 hydroxytryptamine, morepinephrine, and 4-hydroxy-3, 5-dimethoxycinnamic acid.

3. The fungal growth medium of claim 2 wherein said substrate for phenol oxidase is caffeic acid.

4. In a fungal growth media comprising oxgall and caffeic acid the improvement comprising the addition of at least about 0.3 grams per liter of said media of purified saponin which is nontoxic to microbial pathogens.

5. A dry preparation for mixing with water to form a fungal growth media, comprising purified saponin which is nontoxic to microbial pathogens, oxgall, and a substrate for phenol oxidase.

6. The dry preparation of claim 5 and further comprising a supporting agent.

7. The dry preparation of claim 6 wherein said supporting agent is agar.

8. The dry preparation of claim 5 wherein said substrate for phenol oxidase is caffeic acid.

9. A fungal media for the rapid identification of *Cryptococcus neoformans* and *Candida albicans* comprising from about 1 to about 5 weight percent of agar, from about 0.1 to about 1.0 weight percent of purified saponin which is nontoxic to microbial pathogens, from about 0.5 to about 5 weight percent oxgall, and from about 0.005 to about 0.05 weight percent of caffeic acid dissolved in water, said weight percent based upon the water content of the media.

10. The fungal media of claim 9 wherein said agar is present in about 2 weight percent, said purified saponin is present in about 0.5 weight percent, said oxgall is present in about 1 weight percent, and said caffeic acid is present in about 0.03 weight percent.

11. In a method for the identification of *Cryptococcus neoformans* and *Candida albicans* present in a body fluid sample the improvement comprising:
plating said body fluid sample on a fungal growth medium comprising purified saponin which is nontoxic to microbial pathogens, oxgall, and a substrate for phenol oxidase.

12. The method of claim 11 wherein said substrate for phenol oxidase is caffeic acid.

13. In a method for the identification of *Cryptococcus neoformans* and *Candida albicans* present in a body fluid sample wherein said body fluid sample is plated on a primary media for growth and the resulting fungal growth is plated on a secondary media the improvement comprising:
plating said fungal growth on a media comprising purified saponin which is nontoxic to microbial pathogens, oxgall, and a substrate for phenol oxidase, to thereby result in the formation of germ tubes and chlamydospores on said *Candida albicans* and the development of dark pigment by said *Cryptococcus neoformans* without affecting the morphology of other yeasts in said fungal growth.

14. The method of claim 13 wherein said substrate for phenol oxidase is caffeic acid.

15. The method of claim 13 wherein said other yeasts comprise *Candida krusei*.

16. The method of claim 13 wherein said other yeasts comprise *Candida stellatoidea*.

* * * * *

UNITED STATES PATENT AND TRADEMARK OFFICE
CERTIFICATE OF CORRECTION

PATENT NO. : 4,144,133

DATED : March 13, 1979

INVENTOR(S) : Gordon L. Dorn, et al.

It is certified that error appears in the above-identified patent and that said Letters Patent are hereby corrected as shown below:

Column 3, line 34, change "neoforms" to --neoformans--.

Column 4, lines 29-31, change "The purified saponin employed in the fungal media of the subject invention significantly increases the tell-tale brown pigmentation of" from being italicized to regular printing.

Column 8, line 14 (Table 2), change "8.1" to --18.1--.

Column 10, line 18 (column headings) change "Cryphococcus" (first and second occurrences) to --Cryptococcus--.

Column 10, line 2 of "Sample No. 10" change "100% FC" (third occurrence) to --100% F--.

Signed and Sealed this

Twenty-fifth Day of September 1979

[SEAL]

Attest:

LUTRELLE F. PARKER

Attesting Officer   Acting Commissioner of Patents and Trademarks